United States Patent [19]

Baz et al.

[11] Patent Number: 5,849,540
[45] Date of Patent: Dec. 15, 1998

[54] THIODEPSIPEPTIDE ISOLATED FROM A MARINE ACTINOMYCETE

[75] Inventors: Julia Perez Baz; Francisco Romero Millan, both of Leon; Teresa Garcia De Quesada; Dolores Garcia Gravalos, both of Madrid, all of Spain

[73] Assignee: Pharma Mar, S.A., Madrid, Spain

[21] Appl. No.: 936,460

[22] Filed: Sep. 24, 1997

Related U.S. Application Data

[62] Division of Ser. No. 224,628, Apr. 6, 1994, Pat. No. 5,681,813.

[51] Int. Cl.$^6$ .................................................. C12P 21/00
[52] U.S. Cl. ...................... 435/71.3; 435/71.2; 435/71.1; 435/52
[58] Field of Search ................................. 435/71.3, 71.2, 435/71.1, 52

[56] References Cited

U.S. PATENT DOCUMENTS 4,366,309 12/1982 Ganguly et al. .......................... 536/7.1

OTHER PUBLICATIONS

Otsuka et al, The Journal of Antibiotics, Ser. A. pp. 128–131, (May, 1966).
Williamson, et al, the Journal of Antibiotics, vol. XXXV(1), pp. 62–66 (Jan. 1982).
Yoshida et al, Journal of Bacteriology, vol. 93(4), PP. 1327–1331, (1967).
Bergeron et al, Biochemical and Biophysical Res. Comm., vol. 121 (3), pp. 848–854 (Jun. 29, 1984).
Okada et al, The Journal of Antibiotics, vol. 47(2), PP. 129–135, (1994).

*Primary Examiner*—Ponnathapura Achutamurthy
*Assistant Examiner*—T. D. Wessendorf
*Attorney, Agent, or Firm*—Ernest V. Linek; Dike, Bronstein, Roberts & Cushman, LLP

[57] ABSTRACT

The present invention is directed to a novel depsipeptide has been isolated from a new marine strain L-13-ACM2-092 belonging to the family Micromonosporaceae. Its production by aerobic fermentation under controlled conditions of the strain, and the isolation and purification of PM-93135 are described herein. The compound and the fermentation broth demonstrate significant activity against several cancer cell lines. The compound also shows activity against several gram positive bacteria.

3 Claims, 5 Drawing Sheets

THIODEPSIPEPTIDE ISOLATED FROM A MARINE ACTINOMYCETE

This is a divisional of application Ser. No. 08/224,628 filed on Apr. 6, 1994 now U.S. Pat. No. 5,681,813.

FIELD OF THE INVENTION

A novel depsipeptide has been isolated from a new marine strain L-13-ACM2-092 belonging to the family Micromonosporaceae. Its production by aerobic fermentation under controlled conditions of the strain, and the isolation and purification of PM-93135 are described herein. The compound shows good activity against Gram positive bacteria. The compound and the fermentation broth also demonstrate significant activity against several cancer cell lines.

BACKGROUND OF THE INVENTION

Many common bacteria are evolving resistance to more and more antibiotics. According to published reports, resistant bacterial infections killed 19,000 U.S. hospital patients (and contributed to the deaths of 58,000 more) in 1992. For instance, strains of Pneumococcus, which can cause ear infections, meningitis, pneumonia and blood infections, became resistant to penicillin and to four other antibiotics in just the last six years. Some 20 percent of TB microbes resist isoniazid, the treatment of choice, and gonorrhea microbes resist penicillin. More than half the known strains of *Staphylococcus aureus*, which causes blood poisoning, resist everything but vancomycin. Clearly, the need for a constant supply of new antibiotic materials is never ending. Accordingly, one object of the present invention is to provide a new antibiotic agent arbitrarily designated herein as PM-93135.

New antineoplastic compounds are also needed for treatment against several human carcinomas. Accordingly, another object of the present invention is to provide a new antitumor agent, namely the compound PM-93135. This compound is a thiodepsipeptide with significant inhibitory activity of RNA synthesis.

Yet another object of this invention is to provide pharmaceutical compositions for administering to a patient in need of treatment using the active compound described herein. Still another object is directed to the production of the active compound by controlled aerobic fermentation using a biologically pure culture of an organism capable of producing the active compound in appropriate nutrient media, and to methods for the recovery and concentration from the fermentation broth, and to the final purification of the active compound.

SUMMARY OF THE INVENTION

This invention provides a compound with the proposed formula I:

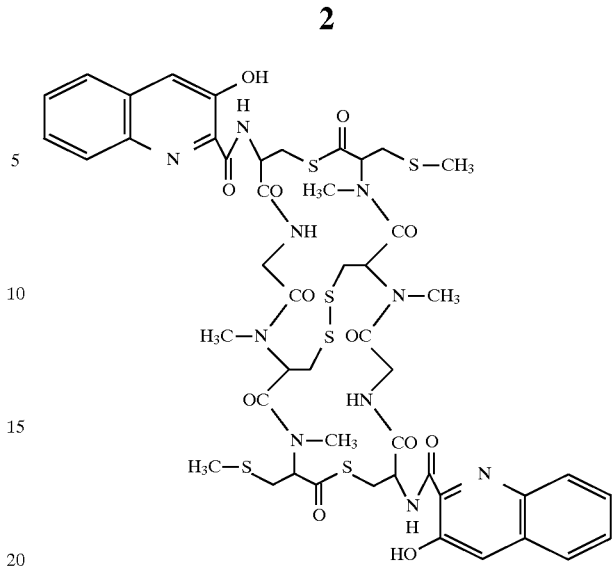

In this invention the process of obtaining PM-93135 is also described, and the preferred process comprises cultivating a strain of a microorganism capable of producing PM-93135 in an aqueous nutrient medium with assimilable carbon and nitrogen sources and salts, under controlled submerged aerobic conditions. The compound PM-93135 is recovered and purified from the cultured broth.

The preferred culture is strain L-13-ACM2-092, and belongs to the family Micromonosporaceae, being taxonomically classified as Micromonospora sp.

As described above, the compound PM-93135 has been found to be effective against several strains of Gram positive and Gram negative bacteria, and it has also been found to have good activity against murine and human tumor cell lines, including P-388, HT-29, A-549 and MEL-28. This compound shows selective activity against RNA synthesis.

DETAILED DESCRIPTION OF THE INVENTION

The Producing Organism

Figure 1:
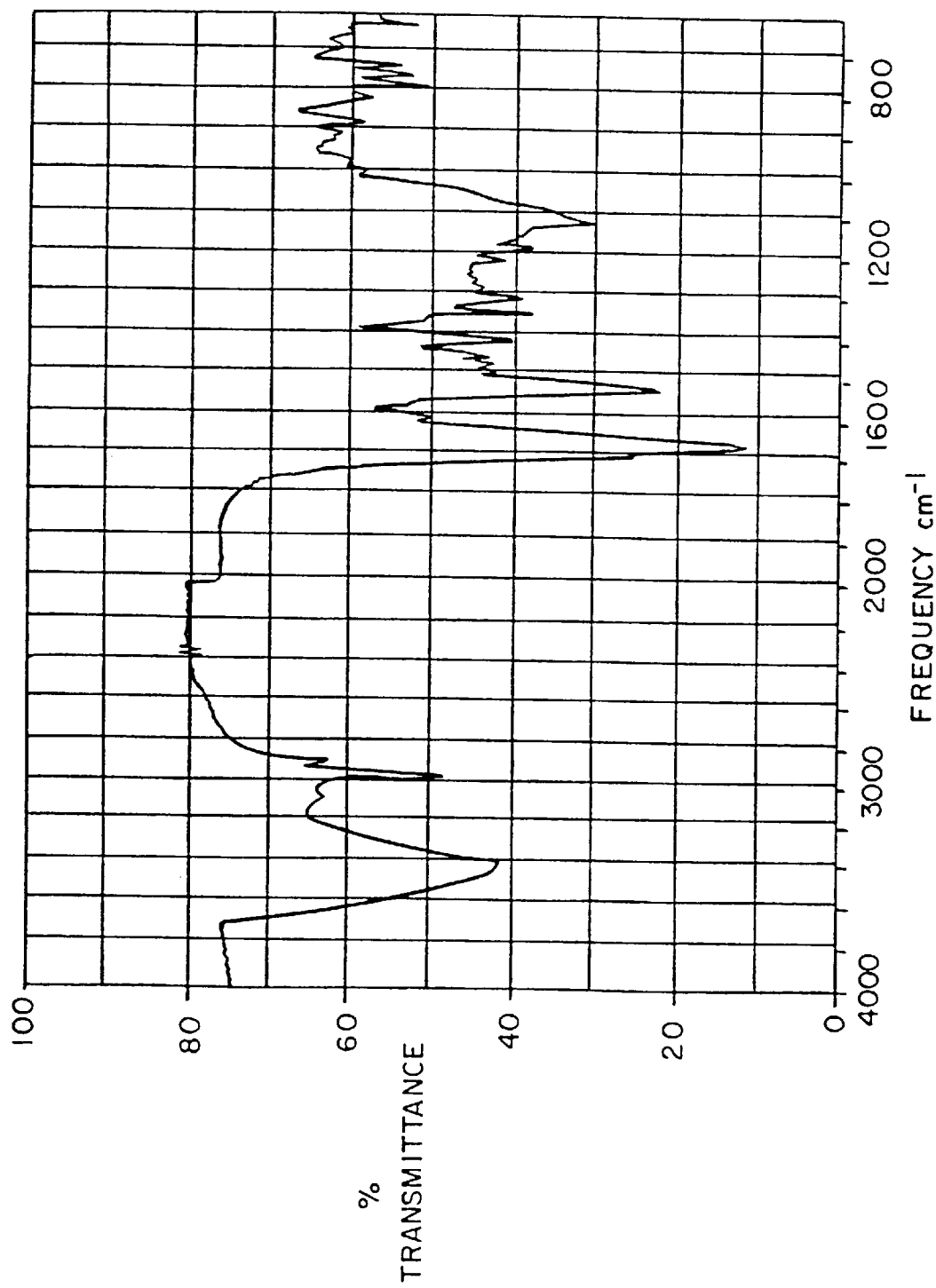
FIG. 1 is an infrared (IR) spectrum of purified PM-93135.

The microorganism utilized for the production of PM-93135 is preferably Micromonospora sp. strain L-13-ACM2-092, a culture of which has been deposited in the Colección Española de Cultivos Tipo at the University of Valencia, Spain under the accession number CECT-3326. This deposit has been made under the provisions of the Budapest Treaty and all restrictions on the availability thereof to the public will be irrevocably revoked upon the granting of a patent on this application.

The organism was isolated from an unidentified marine soft coral collected at the Indian Ocean near the coast of Mozambique. The taxonomic methods described herein are those reported in Table 1.

TABLE 1

1. Colonial morphology
   ISP Media No. 2, 4, 5 and 6, E. B. Shirling & D. Gotlieb., *Int. J. Syst. Bacteriol.,* 16:313, 1966.
   ATCC Medium No. 172, ATCC Catalog.
   Media 172 and ISP with ASW 50%.
   Czapek Agar Difco.
   Bennet Agar, S. A. Waksman, *The Actinomycetes,* Vol. II:331, 1961.
   1.5% Water Agar, G. M. Luedemann, *Personal Communication.*

2. Physiological characteristics
   ISP Medium No. 1, E. B. Shirling and D. Gotlieb. Ibid.
   NaCl Resistance: ATCC 172 with 0, 2, 4, 7 and 10% NaCl.
   Carbon utilization: ISP-9, E. B. Shirling & D. Gotlieb. Ibid.
3. Fatty acids analysis, Van der Auwera et al., *J. Microbiol. Methods,* 4:265, 1986.
4. Whole cell sugar analysis, Guerrant and Moss, *Anal. Chem.,* 56:633, 1984. Hasegawa et al., *J. Gen. Appl. Microbiol.,* 29:319, 1983.
5. Diaminopimelic acids analysis, Hasegawa et al., *J. Gen, Appl. Microbiol.,* 29:319, 1983.

All cultures were incubated at 27° C. and records of results were made weekly up to 21 days.

A Description of the organism is as follows

Morphology

After 21 days at 28° C. good growth is observed in ISP 2 and 172 with ASW. Several shades of orange are observed on the different media studied. No aerial mycelium is formed. Substrate mycelium is branched. Isolated spores over the substrate mycelium occur. The spores are spherical. No other formations were observed except some overgrowth of mycelial mass in some media, and after at least 14 days.

TABLE II

Fatty acids composition of *Micromonospora sp.* CECT-3326 and of several actinomycete strains. Composition is given as percentage of total fatty acids content.

|  | 13:0 | i-14:0 | 14:0 | i-15:0 | a-15:0 | 15:0 | i-16:1 | i-16:0 | 16:1 | 16:0 | i-17:1 | i-17:0 | a-17:0 | 17:1 | 17:0 | i-18:1 | i-18:0 | cis-18:1 | 18:0 |
|---|---|---|---|---|---|---|---|---|---|---|---|---|---|---|---|---|---|---|---|
| ACM2-92 | <1 | 1.00 | <1 | 5.50 | 1.31 | 3.37 | 2.23 | 29.49 | <1 | 1.65 | <1 | <1 | 2.58 | 24.50 | 10.77 | 4.33 | <1 | 2.64 | 1.44 |
| STALBUS | <1 | 6.52 | <1 | 9.88 | 22.92 | <1 | 5.50 | 25.29 | <1 | 3.75 | 1.28 | 3.38 | 8.60 | <1 | <1 | <1 | 1.09 | <1 | <1 |
| SPAMETH | 1.21 | 10.34 | <1 | 1.86 | <1 | 4.30 | <1 | 15.51 | 5.63 | 8.62 | 1.08 | <1 | <1 | 24.02 | 9.43 | 7.11 | <1 | 4.60 | 1.04 |
| SPVIRIDO | <1 | 4.04 | 1.10 | 18.94 | 2.71 | 4.89 | <1 | 26.44 | <1 | 4.43 | <1 | 2.60 | 1.58 | 11.36 | 8.58 | 7.48 | <1 | <1 | 1.16 |
| AMCITRE | <1 | <1 | 3.18 | <1 | <1 | 1.03 | <1 | 6.37 | 12.62 | 40 | <1 | <1 | <1 | <1 | 1.16 | <1 | <1 | 14.25 | 2.82 |
| APBRAZIL | <1 | 3.15 | <1 | 15.46 | 18.91 | 2.76 | <1 | 19.07 | 2.15 | 1.79 | <1 | 2.39 | 9.64 | 11.18 | 2.82 | <1 | <1 | 3.38 | 1.06 |
| AMPDIGIT | <1 | 11.57 | <1 | 11.21 | 9.96 | <1 | 2.87 | 34.23 | <1 | 1.08 | <1 | 1.28 | 5.08 | 4.39 | 1.64 | <1 | 1.76 | 7.60 | 1.54 |
| AMYORIE | <1 | 3.40 | 2.37 | 19.94 | 4.66 | 1.17 | <1 | 11.85 | 5.59 | 18.41 | <1 | 2.99 | 4.44 | 3.09 | 2.73 | <1 | <1 | 6.21 | 3.04 |
| MNCHALC | <1 | 1.68 | <1 | 8.91 | 2.29 | 1.53 | 1.15 | 38.23 | <1 | 1.88 | 1.49 | 2.32 | 2.25 | 5.43 | 6.95 | 14.58 | 1.31 | 1.28 | 2.68 |
| MNECHCA | <1 | 1.17 | <1 | 6.97 | 1.24 | 2.81 | <1 | 30.88 | <1 | 2.29 | 1.63 | 4.11 | 1.68 | 12.15 | 4.90 | 7.23 | <1 | 10.05 | 1.69 |
| MNFUSCA | <1 | <1 | <1 | 26.56 | 6.53 | <1 | <1 | 8.58 | <1 | <1 | 7.30 | 11.89 | 13.25 | 2.90 | 3.37 | 3.59 | <1 | 2.33 | 1.94 |
| SACCAER | <1 | 3.06 | 1.35 | 14.41 | 8.62 | 1.04 | 5.68 | 20.07 | 13.84 | 6.16 | 4.55 | 2.20 | 5.31 | 2.02 | <1 | <1 | <1 | <1 | 1.43 |
| NOAFRI | 1.51 | 5.43 | 3.35 | 4.62 | <1 | 7.46 | 3.09 | 22.18 | 2.69 | 5.15 | 2.35 | <1 | <1 | 8.15 | 4.75 | 17.03 | <1 | <1 | 1.23 |
| MTSALMO | <1 | 1.12 | 1.28 | 6.75 | <1 | 7.83 | 7.53 | 21.58 | 1.21 | 1.97 | 1.01 | <1 | 1.07 | 11.58 | 5.53 | 17.34 | <1 | <1 | <1 |
| MTRUBRA | <1 | 1.40 | 1.38 | 4.12 | <1 | 3.41 | 7.27 | 25.00 | 2.63 | 3.89 | 2.17 | 1.08 | <1 | 6.84 | 4.97 | 15.44 | 1.25 | <1 | 1.61 |
| MTROSEO | 2.03 | 3.65 | 5.14 | 3.86 | <1 | 9.03 | 3.02 | 12.31 | 3.46 | 6.95 | 1.17 | <1 | <1 | 13.51 | 4.46 | 18.67 | <1 | 1.77 | <1 |
| AMROSEO | <1 | 2.19 | 1.24 | 6.73 | 1.09 | 6.94 | 1.43 | 22.21 | 2.21 | 3.61 | 2.74 | 1.03 | <1 | 10.97 | 4.33 | 17.84 | <1 | <1 | <1 |
| MTFERRU | 1.03 | 1.91 | 1.19 | 1.94 | <1 | 6.43 | 4.12 | 21.50 | 2.32 | 2.34 | <1 | <1 | <1 | 23.51 | 5.71 | 12.15 | 1.27 | 1.43 | <1 |

ACM2-92 = *Micromonospora sp* CECT 3326 (L-13-ACM2-092);
AMCITRE = *Actinomadura citrea* DSM 43461;
AMPDIGIT = *Ampullariella digitata* ATCC 15349;
AMROSEO = *Actinomadura roseoviolacea* DSM 43144;
AMYORIE = *Amycolatopsis orientalis* DSM 40040;
APBRAZIL = *Actinoplanes braziliensis* ATCC 25844;
MNCHALC = *Micromonospora chalcea* ATCC 31395;
MNECHCA = *Micromonospora echinospora calichinensis* NRRL 15839;
MNFUSCA = *Micromonospora fusca* NRRL B-3298;
MTFERRU = *Microtetraspora ferruginea* DSM 43553;
MTROSEO = *Microtetraspora roseola* ATCC 33579;
MTRUBRA = *Microtetraspora rubra* ATCC 27031;
MTSALMO = *Microtetraspora salmonea* ATCC 33580;
NOAFRI = *Nocardiopsis africana* DSM 43748;
SACCAER = *Saccharothrix aerocolonigenes* NRRL B-3298;
SPAMETH = *Streptosporangium amethystogenes* DSM 43179;
SPVIRIDO = *Streptosporangium viridogriseum* ATCC 25242;
STALBUS = *Streptomyces albus* DSM 40313

Physiological characteristics

In ISP-1 no diffusible pigments are formed, neither on solid media. Resistance to NaCl is over 4%. The optimum growth temperature range is between 25° and 35° C., but the organism grows well at 45° C. The organism can grow on glucose, sucrose, rhamnose, and D-xylose as the sole carbon source, however, growth on raffinose, inositol, and α-melibiose is negative, and in mannitol, fructose and arabinose is doubtful.

Cell chemical composition

DAP: meso-2,6-Diaminopimelic acid is present in the whole cell hydrolyzate of strain CECT-3326.

Fatty acids: Comparison with other similar strains is described in Table 2.

Sugars: Whole cell sugar patterns shows the presence of xylose, ribose and glucose when analyzed by TLC on cellulose plates. Arabinose is not detected by this technique following the procedure of Hasegawa, et al. (1983). When the whole cell sugars analysis is performed by gas chromatography, traces of arabinose are detected, so that a sugar pattern belonging to group D of Lechevalier, et al. (1971) (xylose+arabinose containing actinomycetes that correspond to the members of the Micromonosporaceae family) can be inferred. Other important sugars detected by gas chromatography are ribose, mannose, galactose, glucose, m-inositol, glucosamine, and mannosamine. Madurose is not detected as a cellular constituent.

Based on the preceding characteristics the culture has been determined to be a species of the genus Micromonospora, with no similarity to any of the known type strains of this genus available in international collections.

While the deposited organism is clearly preferred, the present invention is not restricted or limited to this particular strain or organism. It is the intention of the present inventors to include other PM-93135 producing organisms, strains or mutants within the scope of this invention.

Fermentation

Micromonospora sp. CECT-3326, when cultured under controlled conditions in a suitable nutrient medium produces the compound PM-93135. This strain is preferably grown in an aqueous nutrient medium, under aerobic and mesophilic conditions, preferably between 24° C. and 35° C. at a pH ranging between 6.0 and 8.0. A wide variety of liquid culture media can be utilized for the cultivation of the organism. Useful media are those that include an assimilable carbon source, such as starch, dextrins, sugar molasses, glycerol, glucose, sucrose, and the like, an assimilable nitrogen source such as protein, protein hydrolysate, defatted meals, corn steep, and the like, and useful inorganic anions and cations such as sodium, magnesium, potassium, ammonium, sulfate, chloride, phosphate, carbonate, and the like. Trace elements may be added also. Aeration is preferably achieved by supplying air to the fermentation medium. Agitation is preferably provided by a mechanical impeller. Conventional fermentation tanks have been found to be well suited for carrying out the cultivation of this organism. The addition of nutrients and pH control as well as antifoaming agents during the different stages of fermentation may be needed for increasing production and void foaming.

The required steps needed for the production of PM-93135 by the preferred organism are:

Start with either frozen or lyophilized mycelium. Obtain the mycelial mass culturing the initial cells in shake flasks with a culture medium containing some of the ingredients described above at mesophilic temperatures and under aerobic conditions. This step may be repeated several times as needed and the material collected will be used as an inoculum to seed one or several fermentation tanks containing the appropriate culture medium. If desired these tanks can be utilized also as inoculum, and this step can be repeated several times if needed, or they can serve as the production stage, depending on the broth volume needed. Sometimes the production medium may be different from the medium one used as the inoculum.

In Table 3 typical media are described that can be used for inoculum development and production of PM-93135:

TABLE 3

| Inoculum medium: | | Production medium: | |
|---|---|---|---|
| Glucose | 5 g | Glucose | 5 g |
| Starch | 20 g | Starch | 20 g |
| Beef extract | 3 g | Soybean meal | 15 g |
| Yeast extract | 5 g | Yeast extract | 5 g |
| Tryptone | 5 g | Tryptone | 2 g |
| $CaCO_3$ | 4 g | $CaCO_3$ | 4 g |
| NaCl | 4 g | NaCl | 4 g |
| $Na_2SO_4$ | 1 g | $Na_2SO_4$ | 1 g |
| KCl | 0.5 g | KCl | 0.5 g |
| $MgCl_2$ | 2 g | $MgCl_2$ | 2 g |
| $K_2HPO_4$ | 0.5 g | $K_2HPO_4$ | 0.5 g |
| Tap water to | 1,000 ml | Tap water to | 1,000 ml |

Production of PM-93135 can be monitored by whole broth assay against murine leukemia P-388 or HPLC.

Isolation of PM-93135

Antibiotic PM-93135 is isolated from the mycelial cake with a suitable organic solvent such as ethyl acetate. The extracts from one or several repeated extractions are combined and evaporated to dryness in vacuo.

Separation and purification of PM-93135 from the crude active extract can be performed by the use of the proper combination of known techniques, as for example, column chromatography, thin layer chromatography (TLC), preparative thin layer chromatography, high pressure liquid chromatography (HPLC), etc.

Fractionation can be guided by antitumoral activity, or TLC visualized with UV light at 366 nm, or analytical HPLC with diode array detection. HPLC analysis are performed at room temperature (Waters RCM 8×10, 8C18 10 cartridge using as mobile phase methanol/water 9:1 and a flow rate of 2 mL/min and plotted at 250 nm. With these conditions PM-93135 retention time is 2.25 min.

On the basis of detailed analysis of their various spectral characteristics, the pure compound can be identified as PM-93135 (see data reproduced in FIGS. 1 to 5).

The infrared absorption spectrum in KBr is shown in FIG. 1 of the accompanying drawings. The following absorption maxima ($cm^{-1}$) are observed: 3370, 1650, 1515, 1095.

Figure 2:
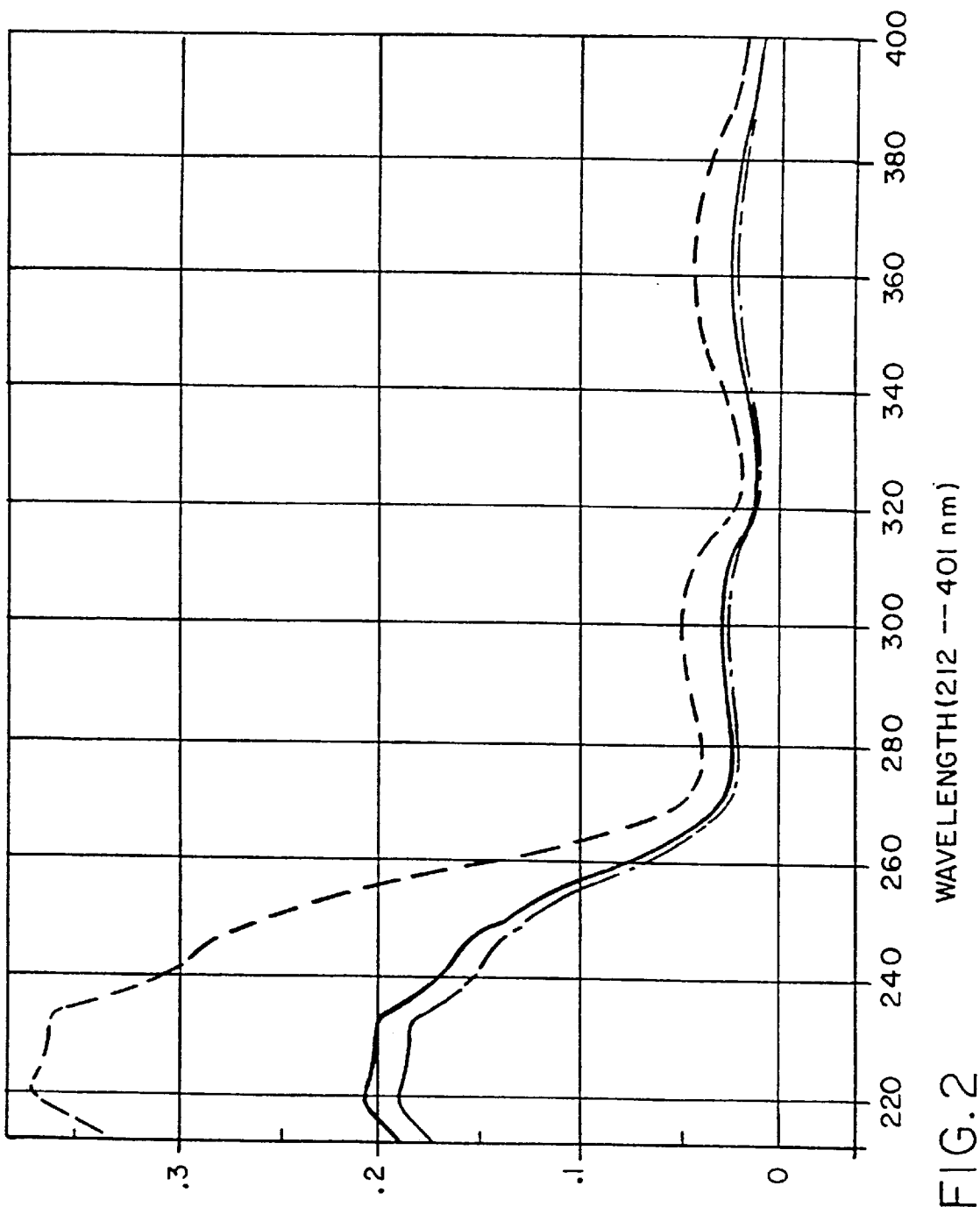
FIG. 2 is an ultraviolet (UV) spectrum of purified PM-93135.

The U.V. spectrum shows absorption at about 220, 230, 300 and 360 mn in $MeOH/H_2O$ 9:1 and is reported in FIG. 2.

Figure 3:
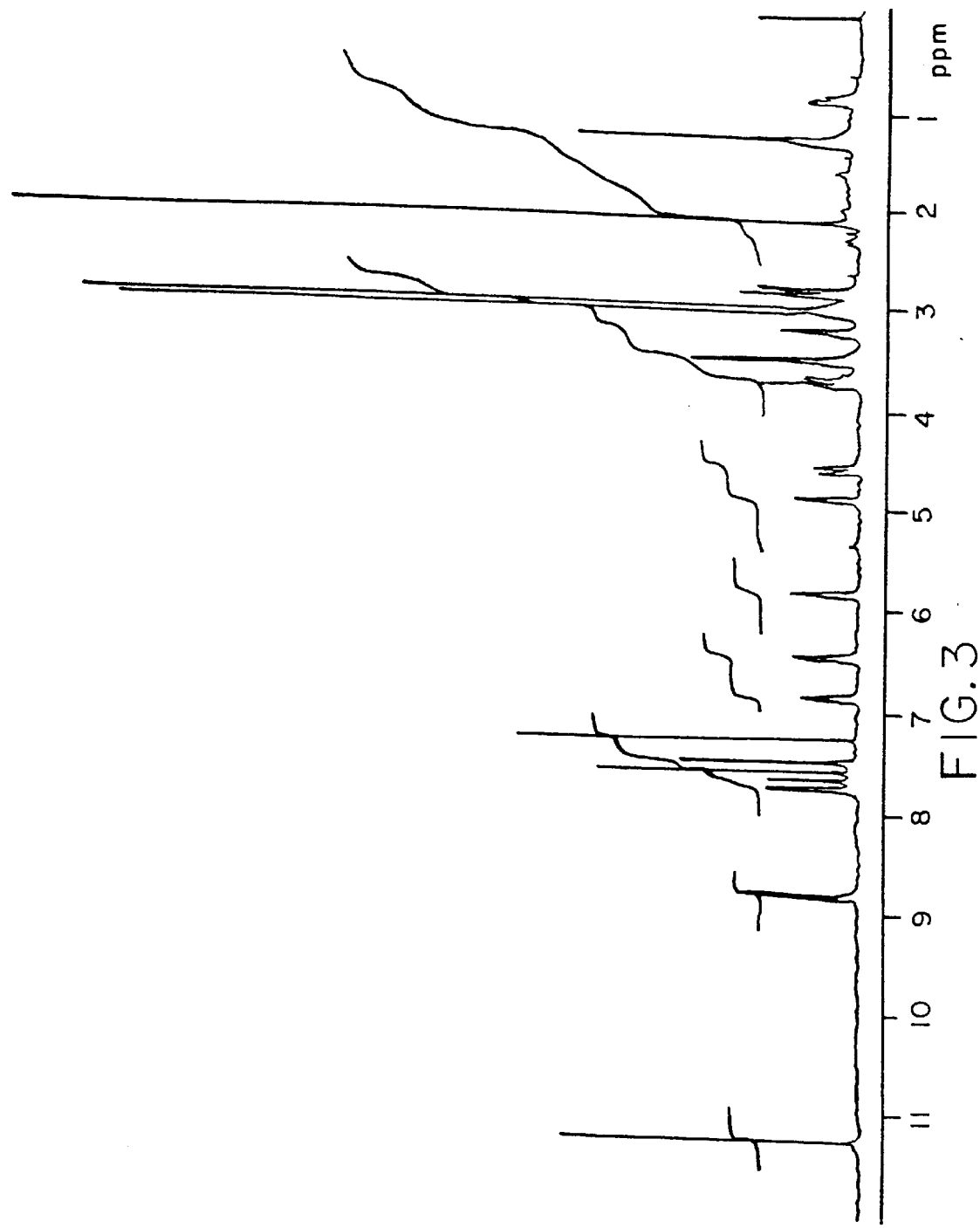
FIG. 3 is a proton NMR ('H) spectrum of purified PM-93135.
Figure 4:
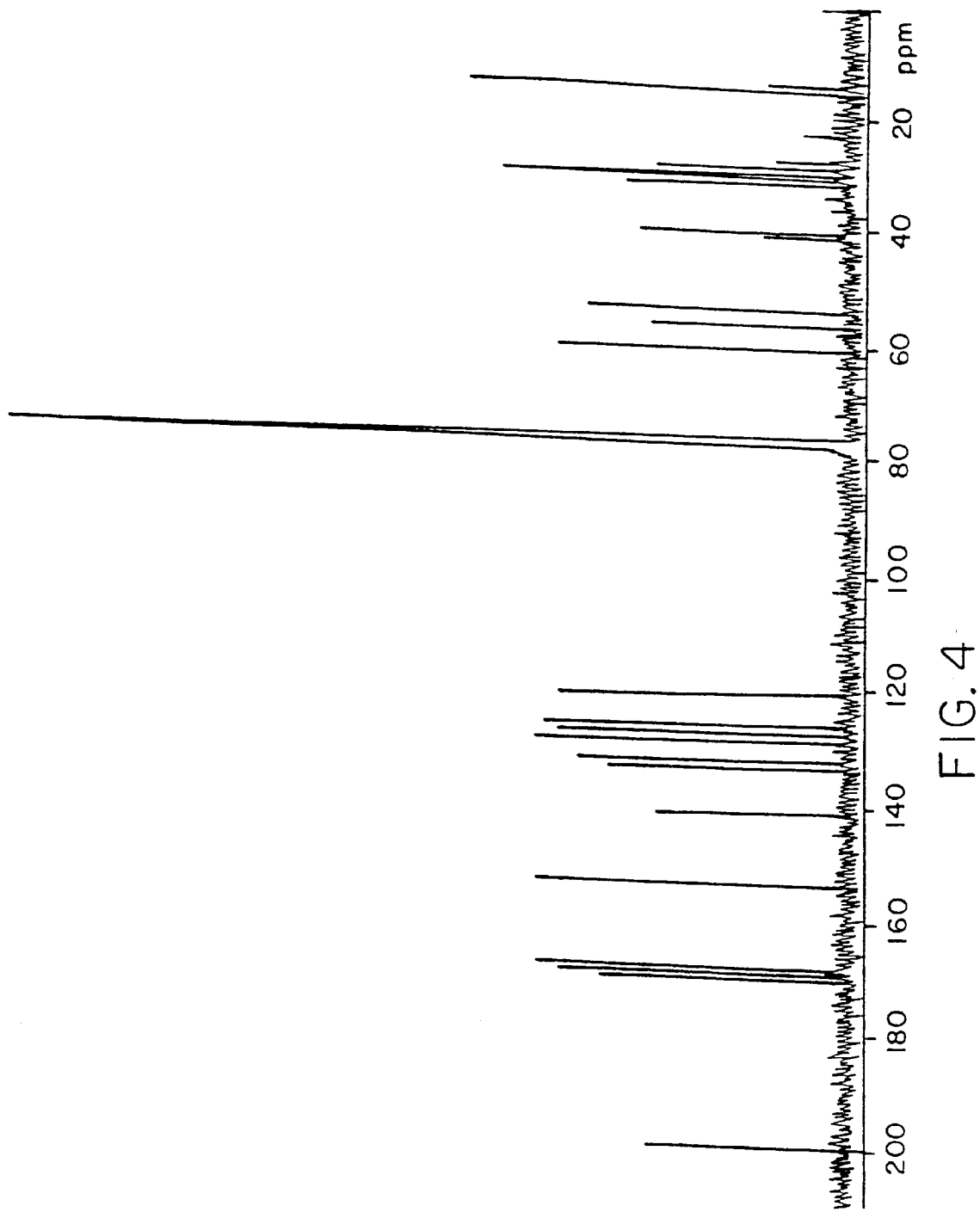
FIG. 4 is a carbon-13 NMR ($^{13}$C) spectrum of purified PM-93135.

The $^1H$ and $^{13}C$ N.M.R. spectra are reported in FIG. 3 and FIG. 4 respectively and show peaks listed in Table 4.

TABLE 4

| C/H | $^1H$ | $^{13}C$ |
|---|---|---|
| 1 | | 199.6 s |
| 2 | 5.80m, 1H(J=4.3, 11.7) | 60.8 d |
| 3 | | 170.0 s |
| 4 | 6.43m, 1H(J=5.6, 9.0) | 56.3 s |
| 5 | | 168.2 s |
| 6 | 3.70m, 1H(J=2.9, 16.6) | 40.3 t |
| | 4.56m, 1H(J=7.5, 16.8) | |
| 7-NH | 6.82m, 1H(J=3.1, 7.3) | |
| 8 | | 169.2 s |
| 9 | 4.89m, 1H(J=4.9, 8.8) | 53.9 d |
| 10-NH | 8.80d, 1H(J=6.1) | |
| 11 | | 169.2 s |
| 12 | 2.85m, 1H(J=11.7, 14.4) | 32.0 t |
| | 3.22m, 1H(J=4.3, 14.14) | |
| 13 | 2.13s, 3H | 15.1 q |

TABLE 4-continued

| C/H | $^1$H | $^{13}$C |
|---|---|---|
| 14 | 3.05s, 3H | 30.7 q |
| 15 | 2.85m, 1H(J=5.6, 14.4) | 41.2 t |
|  | 3.50m, 1H(J=9.2, 13.9) |  |
| 16 | 3.00s, 3H | 30.5 q |
| 17 | 3.50m, 1H(J=9.2, 13.9) | 30.2 t |
|  | 3.70m, 1H(J=4.9, 14.1) |  |
| 2' |  | 133.6 s |
| 3' |  | 153.5 s |
| 3'-OH | 11.26s, 1H |  |
| 4' | 7.58s, 1H | 120.8 d |
| 4a' |  | 132.1 s |
| 5' | 7.73m, 1H | 128.9 d |
| 6' | 7.48m, 1H(J=5.8) | 127.7 d |
| 7' | 7.48m, 1H(J=5.8) | 128.7 d |
| 8' | 7.66m, 1H(J=4.3, 5.1) | 126.6 d |
| 8a' |  | 141.2 s |

Figure 5A:
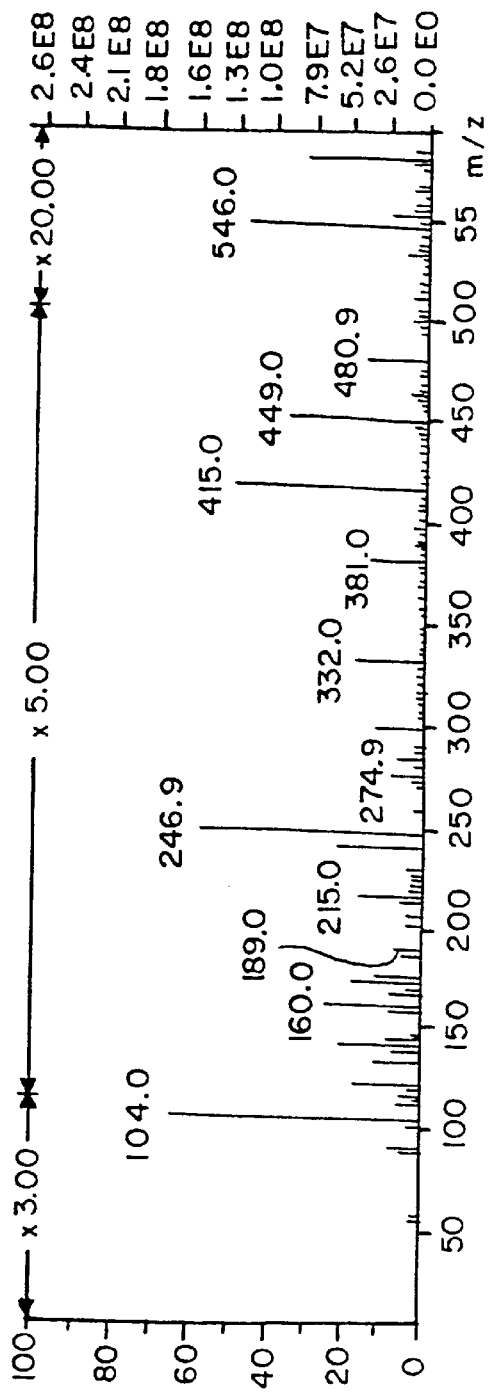
FIG. 5 is the mass spectrum of purified PM-93135.
Figure 5B:
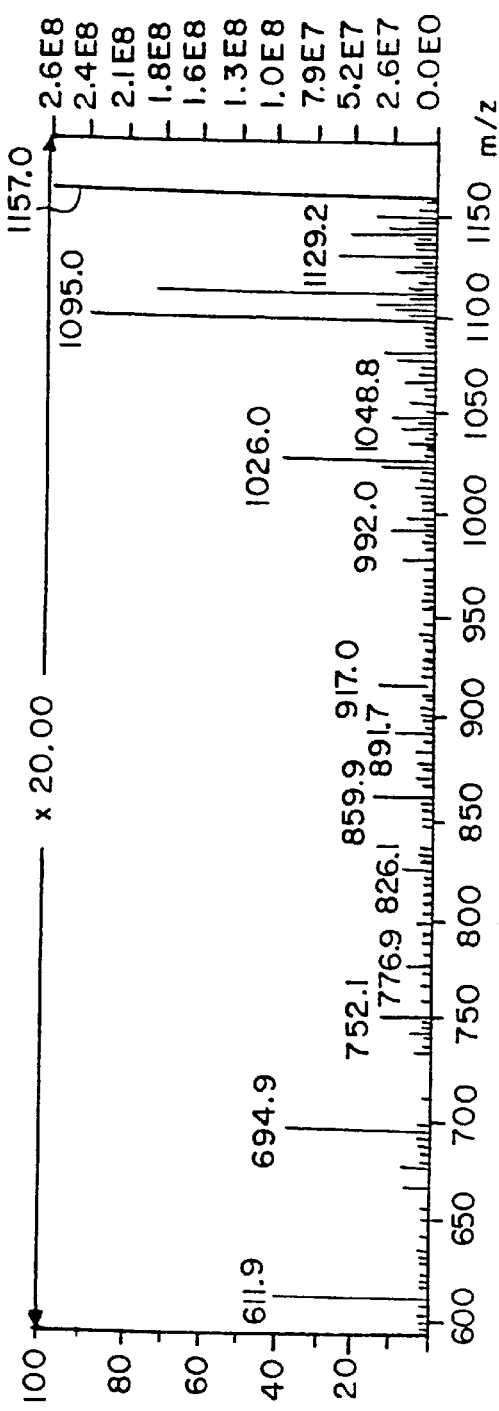

The mass spectrum is shown in FIG. 5. The main peaks are the following (the first number is the rate m/z and the second in parenthesis the percentage of relative abundance):

104(100); 246.9(51); 415(43); 449(31); 546(10); 580(7); 611(7); 694(8); 1026(11); 1095(20); 1109(16); 1157(22).

Biological activity of PM-93135:

The antimicrobial activity of compound PM-93135 was studied by incubating the tested microorganisms with PM-93135 in liquid Mueller-Hinton medium at 37° C. The minimum inhibitory concentration (MIC) was determined by the appearance of turbidity in the incubating medium after 24 hours of incubation with PM-93135. In Table 5 these results are shown. PM93135 shows bactericidal activity against Gram positive bacteria.

TABLE 5

| Microorganism | MIC (g/ml) |
|---|---|
| Escherichia coli | >100 |
| Klebsiella pneumoniae | >100 |
| Pseudomonas aeruginosa | >100 |
| Staphylococcus aureus | 0.05 |
| Bacillus subtilis | 0.05 |
| Micrococcus luteus | 0.03 |

The antitumor activities of PM-93135 have been determined "in vitro" in cell cultures of mouse leukemia P-388, human lung carcinoma A-549, human colon carcinoma HT-29 and human melanoma MEL-28. The procedure was carried out using the methodology described by Bergeron, et al., Biochem. Biophys. Res. Comm., 121:848, 1984 and by Schroeder, et al., J. Med. Chem., 24:1078, 1981. The IC$_{50}$ found was of 0.002, 0.002, 0.01, and 0.0025 g/ml respectively.

PM-93135 was found to inhibit RNA synthesis with an IC$_{50}$ of 0.008 g/ml. The concentration to reach the same level of inhibition for DNA was found to be 50 times higher (0.4). These studies were carried out using P-388 cells, and the inhibition was followed by estimating the incorporation of ($^3$H)thymidine of DNA and ($^3$H)uridine for RNA.

The compound of the present invention exhibits antitumor activity against mammalian tumors such as P-388 murine leukemia, A-549 human lung carcinoma, HT-29 human colon carcinoma, and MEL-28 human melanoma. Also provides a method of treating any mammal affected by a malignant tumor sensitive to PM-93135, which comprises administering to the affected individual a therapeutically effective amount of PM-93135 or a pharmaceutical composition thereof.

The present invention also relates to pharmaceutical preparations which contain as active ingredient compound PM-93135, or a pharmaceutical acceptable acid addition salt thereof, as well as the processes for its preparation.

Examples of pharmaceutical compositions include any solid (tablets, pills, capsules, granules, etc.) or liquid (solutions, suspensions or emulsions) with suitable composition or oral, topical or parenteral administration, and they may contain the pure compound or in combination with any carrier or other pharmacologically active compounds. These compositions may need to be sterile when administered parenterally.

The correct dosage of a pharmaceutical composition comprising PM-93135 will vary according to the particular formulation, the mode of application, and the particular situs, host and bacteria or tumor being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

The present invention will be further illustrated with reference to the following examples which aid in the understanding of the present invention, but which are not to be construed as limitations thereof. All percentages reported herein, unless otherwise specified, are present by weight. All temperatures are expressed in degrees Celsius. All incubations are carried out at 28° C. and flasks are shaken in an orbital shaker at 250 rpm. All media and recipients are sterile and all culture processes aseptic.

EXAMPLE 1

Stock Culture; Whole broth of a pure culture of Micromonosora sp. L-13-ACM2-092 strain (CECT-3326) is preserved frozen in 20% glycerol.

Inoculum: A frozen culture or a well grown slant culture (5% vol) is used to seed 100 mL of seed medium described previously in a 250 cc shake flask. The flask is incubated during 48 hrs. 500 mL of the same medium in a 2 L Erlenmeyer flask are seeded with 10% of the first stage inoculum. The flask is incubated during 48 h.

Fermentation: With 2.5 L of second stage inoculum seed 50 L of production medium already described contained in a 75 L fermentation tank. The fermentation is carried out during 96 hours with 400 rpm agitation and air flow of 0.5 V/M.V.

Monitor secondary metabolite production by assay of whole broth against P-388 or by HPLC.

Isolation: Whole harvested broth (45 L) is filtered to separate biomass and other solids, the mycelial cake is extracted three times with 7L ethyl acetate each. The extracts are combined, desiccated with sodium sulfate, and evaporated to dryness in vacuo to yield 4 g of crude solid.

This solid is subjected to silica gel column chromatography using a mixture of chloroform/methanol as the eluting solvent. The antitumor activity is detected in fractions 3–4 (1.3 g) and eluted with chloroform/methanol 90:10 to 85:15. An aliquot of this material (400 mg) is further purified by preparative thin layer chromatography and developed with chloroform/methanol (95:5-v/v) to yield 150 mg of pure PM-93135.

Cited References

The following references have been cited herein, and they are hereby incorporated herein by reference:

(1) American Type Culture Catalog, 17th edition, 1989. Rockville, Md. U.S.A.;
(2) Bergeron et al., Biochem. *Biophys. Res. Comm.,* 121:848 (1984);
(3) Guerrant G. O. and C. W. Moss., *Anal Chem.,* 56-663 (1984);
(4) Hasegawa et al., *J. Gen. Appl Microbiol.,* 29:319 (1983);
(5) Lechevalier et al., *J. Bacteriol.,* 105:313 (1971);
(6) Schroeder et al., *J. Med. Chem.,* 24:1078 (1981);
(7) Shirling B. E. and D. Gottlieb, *Int. J. Syst. Bacteriol.,* 16:313 (1966);
(8) Van der Auwera et al., *J. Microbiol. Methods,* 4:265 (1986); and
(9) Waksman S. A., *The Actinomycetes,* Vol. II: 331 (1961).

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. A process for producing the compound PM-93135, which has the following structure:

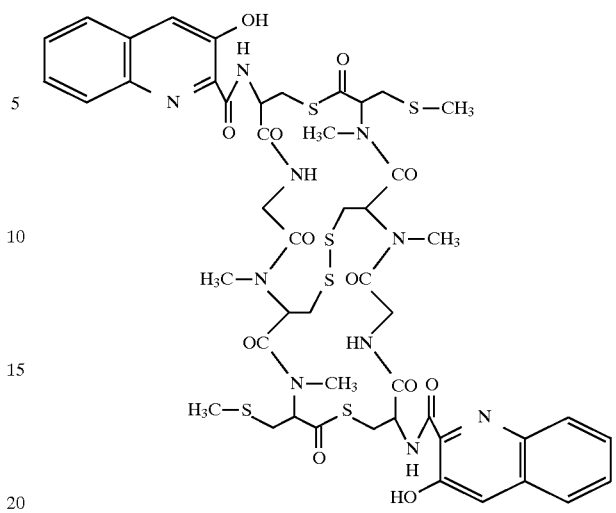

said process comprising cultivating a strain of a microorganism capable of producing the compound PM-93135 in an aqueous nutrient medium with assimilable sources of carbon and nitrogen, under controlled submerged aerobic conditions;
wherein the PM-93135 producing microorganism is the substantially pure culture strain L-13-ACM2-092, available under accession No. CECT-3326, from the Colección Española de Cultivos Tipo at the University of Valencia, Spain.

2. The process of claim 1, which further comprises isolating and purifying the compound PM-93135 from the aqueous nutrient medium.

3. The substantially pure culture strain L-13-ACM2-092 as isolated from marine soft coral, which belongs to the family Micromonosporaceae, and has been taxonomically classified as a Micromonospora sp.

* * * * *